United States Patent [19]
Haissaguerre et al.

[11] Patent Number: 5,931,811
[45] Date of Patent: Aug. 3, 1999

[54] STEERABLE CATHETER WITH FIXED CURVE

[75] Inventors: Michel Haissaguerre, Talence, France; Gary S. Falwell, Manchester, N.H.

[73] Assignee: C.R. Bard, Inc., Murray Hill, N.J.

[21] Appl. No.: 09/018,223

[22] Filed: Feb. 3, 1998

Related U.S. Application Data

[63] Continuation of application No. 08/739,145, Oct. 28, 1996, Pat. No. 5,779,669.

[51] Int. Cl.⁶ .................................................. A61M 37/00
[52] U.S. Cl. ............................ 604/95; 604/500; 604/528; 604/532
[58] Field of Search ............................... 604/95, 500, 507, 604/508, 510, 523, 528, 530, 532

[56] References Cited

U.S. PATENT DOCUMENTS 5,779,669   7/1998   Haissaguerre et al. .................... 604/95

FOREIGN PATENT DOCUMENTS

| | | |
|---|---|---|
| 0 600 676 | 11/1993 | European Pat. Off. . |
| 38 19 372 | 1/1990 | Germany . |
| WO 94/24930 | 11/1994 | WIPO . |
| WO 96/32980 | 10/1996 | WIPO . |
| WO 96/34646 | 11/1996 | WIPO . |
| WO 97/18853 | 11/1996 | WIPO . |

*Primary Examiner*—John D. Yasko
*Attorney, Agent, or Firm*—Darby & Darby

[57] ABSTRACT

A steerable catheter is disclosed which includes a complexly curved proximal section shaped to seat the catheter relative to an anatomical feature within a patient. The catheter also includes a flexible intermediate section which has comparatively greater flexibility than other sections of the catheter. The flexible intermediate section bends in response to forces applied by an attached steering device and substantially all of the flex in the catheter may be contained within the flexible intermediate section. The catheter further has a pre-shaped distal section which is urged into contact with tissue within the patient when the flexible intermediate section flexes. In a preferred embodiment, the distal section supports a plurality of ring electrodes and is shaped to generally correspond to the physiology of a wall of the heart.

10 Claims, 6 Drawing Sheets

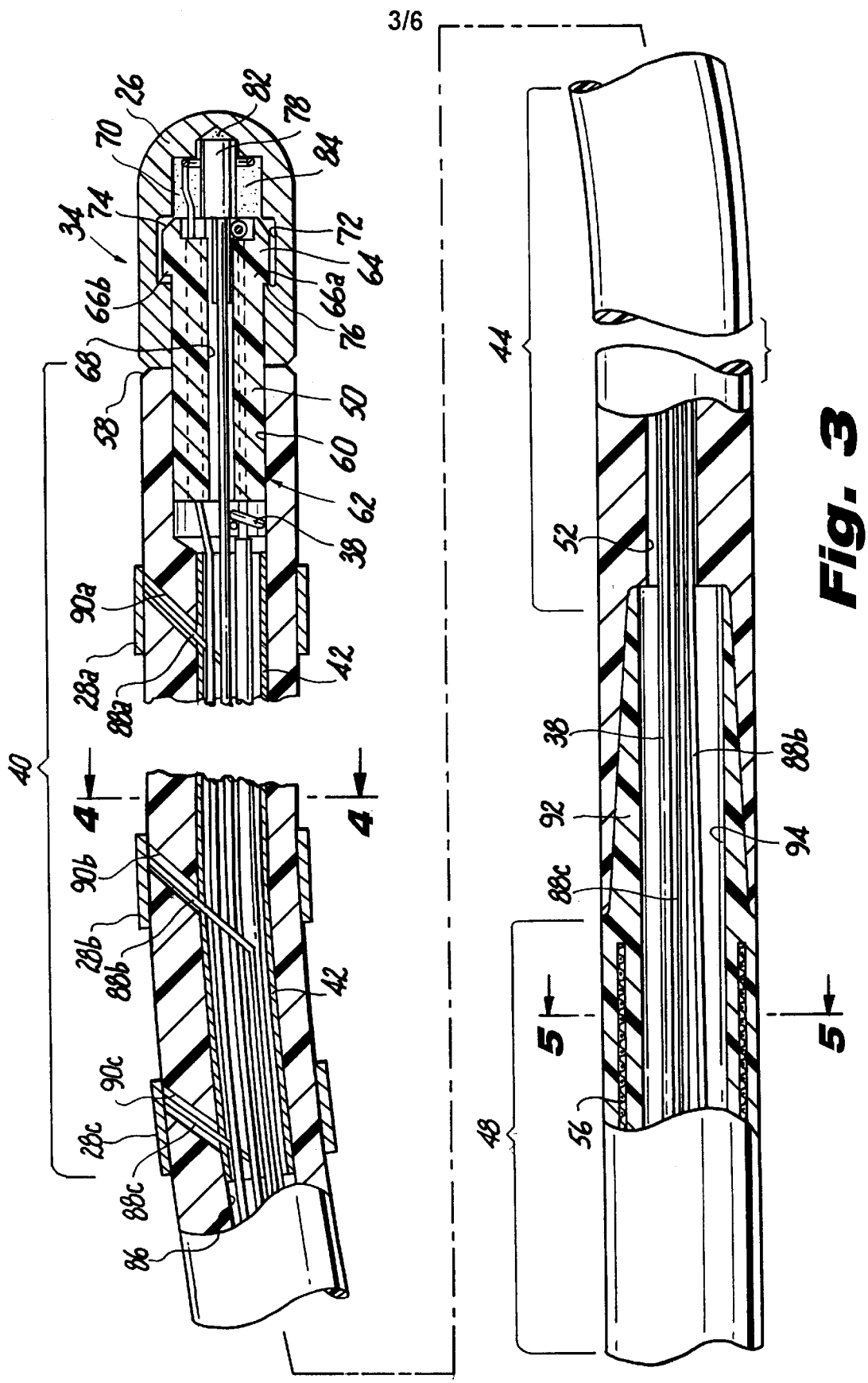

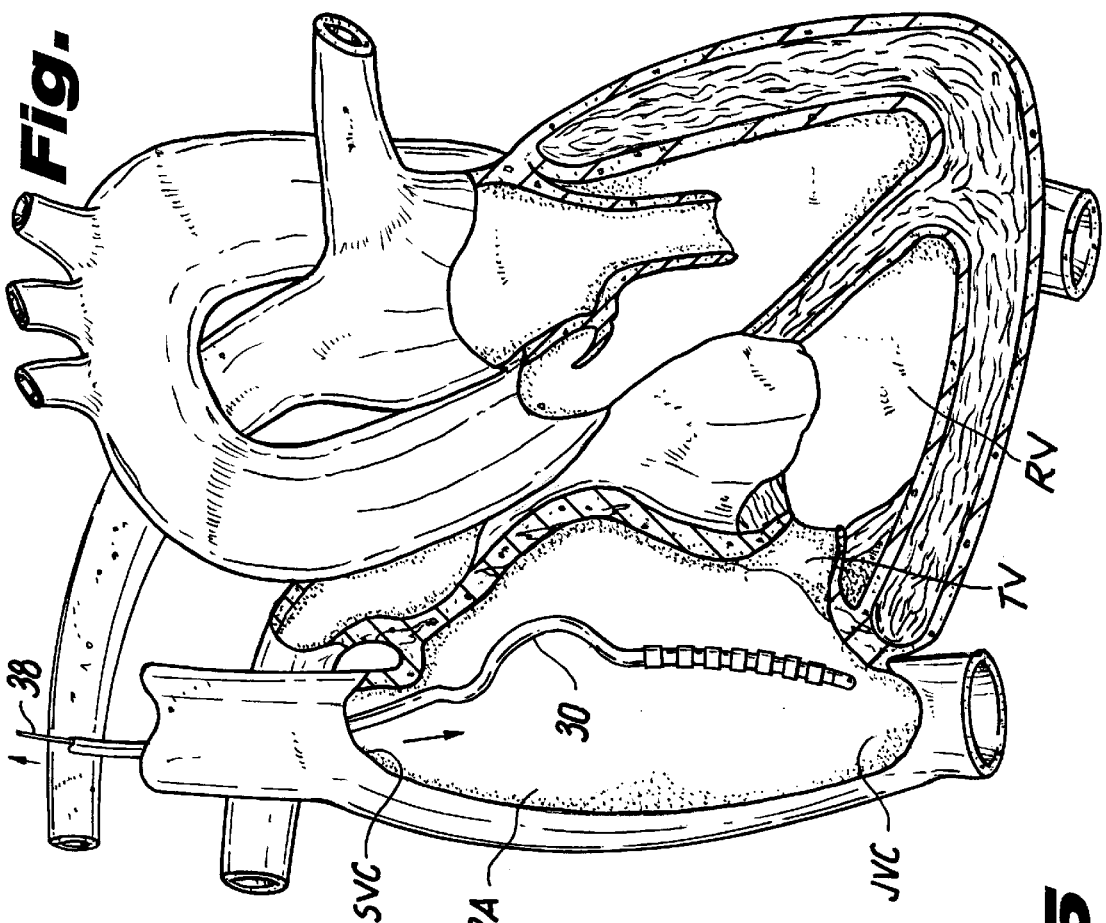
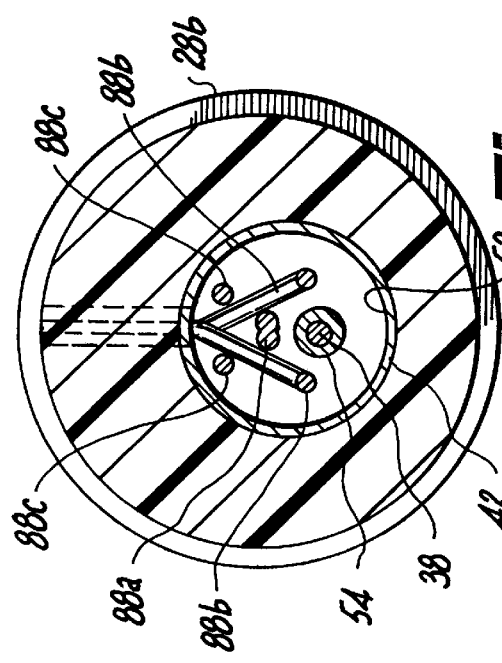
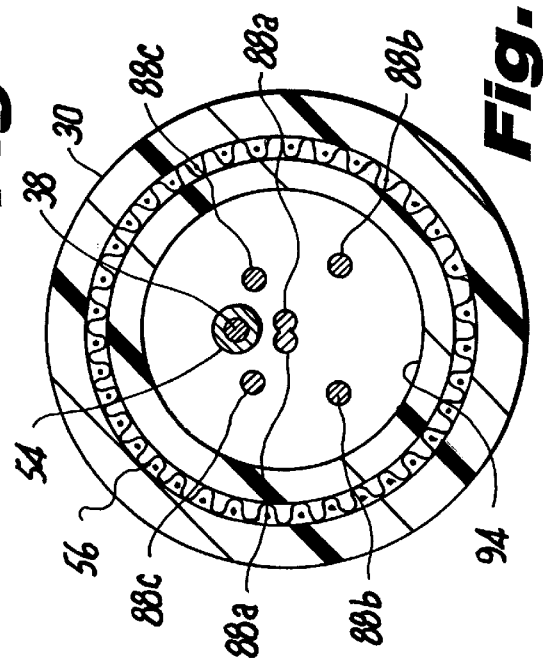

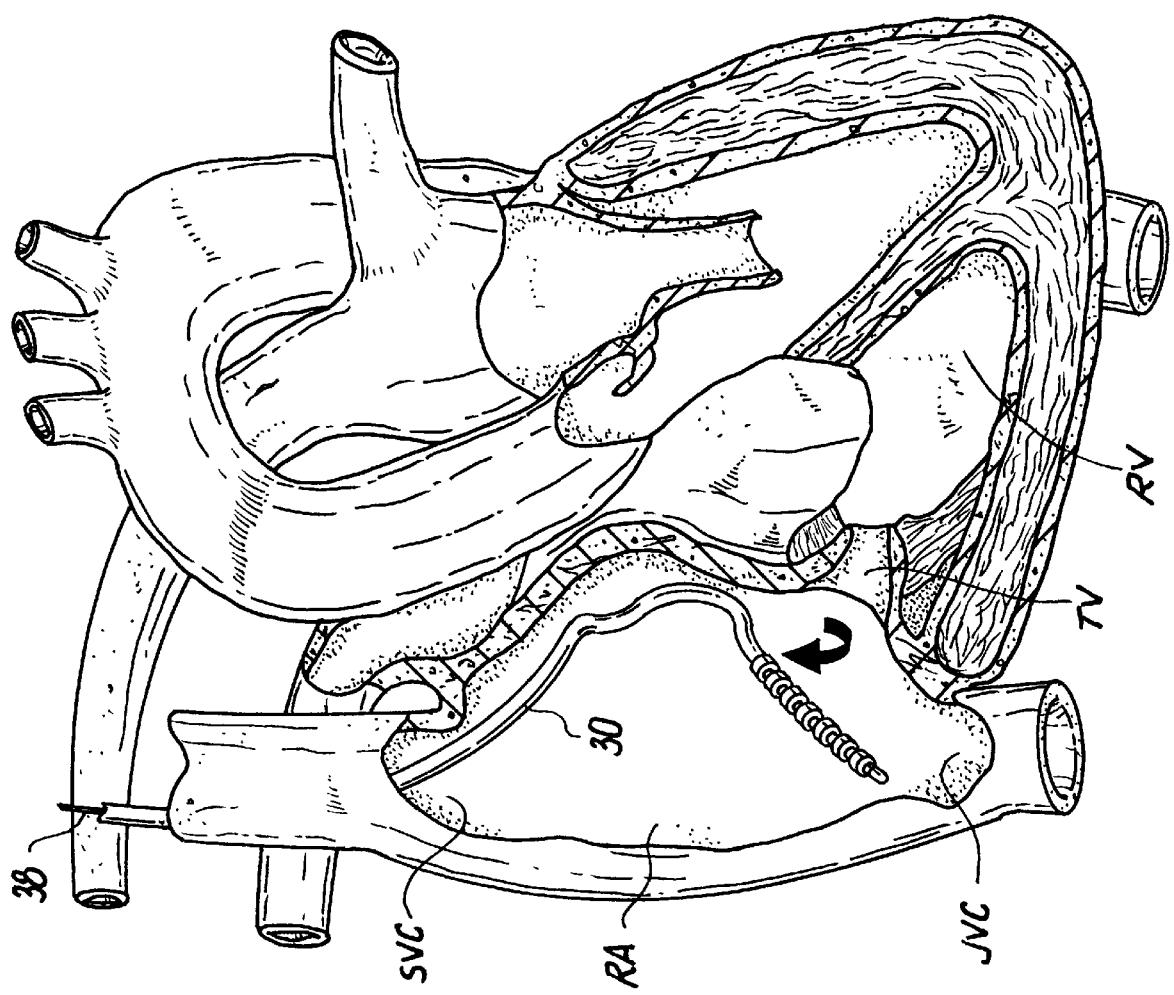

STEERABLE CATHETER WITH FIXED CURVE

This is a continuation of application Ser. No. 08/739,145, filed Oct. 28, 1996 now U.S. Pat. No. 5,779,669. Each of these prior applications is hereby incorporated herein by reference, in its entirety.

FIELD OF THE INVENTION

This invention relates to medical catheters and, more particularly, to medical catheters having a portion shaped to ensure that a distal portion is positioned within the right atrium of a heart.

BACKGROUND OF THE INVENTION

Medical catheters have been used to access locations within a patient without invasive surgery. The catheter may be introduced into a body passageway at locations where the passageway is near the skin. The catheter can then be advanced to an area of interest. Often, the ability to control the exact position and orientation of the tip of a catheter largely determines the usefulness of the catheter.

One known application for medical catheters is for the recording and mapping of endocardial signals, for example, to identify the focus or foci of a dysrhythmia or to ablate endo- or myocardial tissue. The success and advancement of current techniques has been dependent upon the development and use of more precise techniques for locating arrhythmogenic sites. Further, the operator (e.g., electrophysiologist) has had to compromise between placing the catheter in the place of greatest clinical interest verses placing the catheter in areas which are anatomically accessible.

To assist positioning a catheter at a desired location within a body, pre-shaped catheters have been constructed. Known catheters have been shaped to specifically access a particular site within the body. For example, U.S. Pat. No. 4,882,777 of Narula discloses a catheter having a complex multi-planar curvature which automatically positions the distal end of the catheter at a desired internal location. This particular catheter is designed to traverse the inferior vena cava through the tricuspid valve and into the right ventricle from the right atrium. Another catheter containing pre-shaped sections is disclosed in U.S. Pat. No. 5,423,772 of Lurie et al. That catheter has a distal portion containing a first longitudinal curve of a radius between 7.0 cm and 11.0 cm and a second longitudinal curve of between 0.5 cm and 2.0 cm. Both of these longitudinal curves are curved in the same direction. Other examples of the preshaped catheters are shown in U.S. Pat. Nos. 3,485,234 and 3,503,385, both of Stevens, U.S. Pat. No. 3,729,008 of Berkovits, and U.S. Pat. No. 4,860,769 of Forgerty, each of which is hereby incorporated by reference as if set forth in their entireties herein.

Steerable catheters have also been used to direct the catheter to a desired location, and properly orient or position the catheter at the desired location. For example, U.S. Pat. No. 5,327,905 of Avitall discloses a pre-formed catheter section designed to be steered into a position on either the atrial or ventricular side of the A-V ring. Other steerable catheter designs are disclosed in, for example, U.S. Pat. No. Re. 34,502 of Webster, Jr. and U.S. Pat. No. 4,920,980 is of Jackowski.

The object of this invention, therefore, is to provide a catheter which is capable of being properly positioned against the wall of the right atrium.

A further object of the invention is to provide a catheter which may be nested within the tricuspid valve without prolapsing through the valve as the catheter is rotated during use.

SUMMARY OF THE INVENTION

According to one aspect of the invention, a steerable catheter is disclosed which includes a complexly curved proximal section which is shaped to seat the catheter relative to an anatomical feature within a patient, such as the annulus of the tricuspid valve. The steerable catheter also includes a flexible intermediate section which has comparatively greater flexibility than other sections of the steerable catheter. The flexible intermediate section bends in response to forces applied by an attached steering device and substantially all of the flex in the catheter may be contained within the flexible intermediate section. A preshaped distal section is urged into contact with tissue within the patient when the flexible intermediate section flexes.

In one embodiment of the invention, the distal section supports a plurality of ring electrodes and is shaped to generally correspond to the physiology of the inner wall of the right atrium of the heart.

According to another aspect of the invention, a method of positioning a catheter is disclosed in which a steerable catheter is positioned relative to an anatomical feature within the patient. The method comprises providing a steerable catheter generally constructed in accordance with the invention. The steerable catheter is advanced into the patient until a complexly curved section of the catheter is seated relative to the anatomical feature within the patient. The complexly curved section should generally correspond in shape to the anatomical feature against which the catheter is to be seated. Once seated, a pulling force is applied to a wire to cause a flexible intermediate section of the catheter to flex and thereby entrain a distal end of the catheter into contact with a desired site within the patient.

Further features and advantages of the invention are described in connection with the following detailed description of a presently preferred embodiment.

BRIEF DESCRIPTION OF THE DRAWINGS

The foregoing and other features of the present invention will be more readily apparent from the following detailed description and drawings of an illustrative embodiment of the invention in which:

FIG. 3 is a cross-sectional view taken along line 3—3 of FIG. 2;

FIG. 4 is a cross-sectional view taken along line 4—4 of FIG. 3;

FIG. 5 is a cross-sectional view taken along line 5—5 of FIG. 3;

FIG. 6 is a view of the right atrium of the heart with parts broken away showing the catheter of FIG. 1 being advanced therein from the superior vena cava in a stressed (steered) condition;

FIG. 7 is a view of the right atrium of the heart with parts broken away showing the catheter of FIG. 1 returning to its unstressed condition (no pulling force being applied)

DESCRIPTION OF A PREFERRED EMBODIMENT

Figure 1:
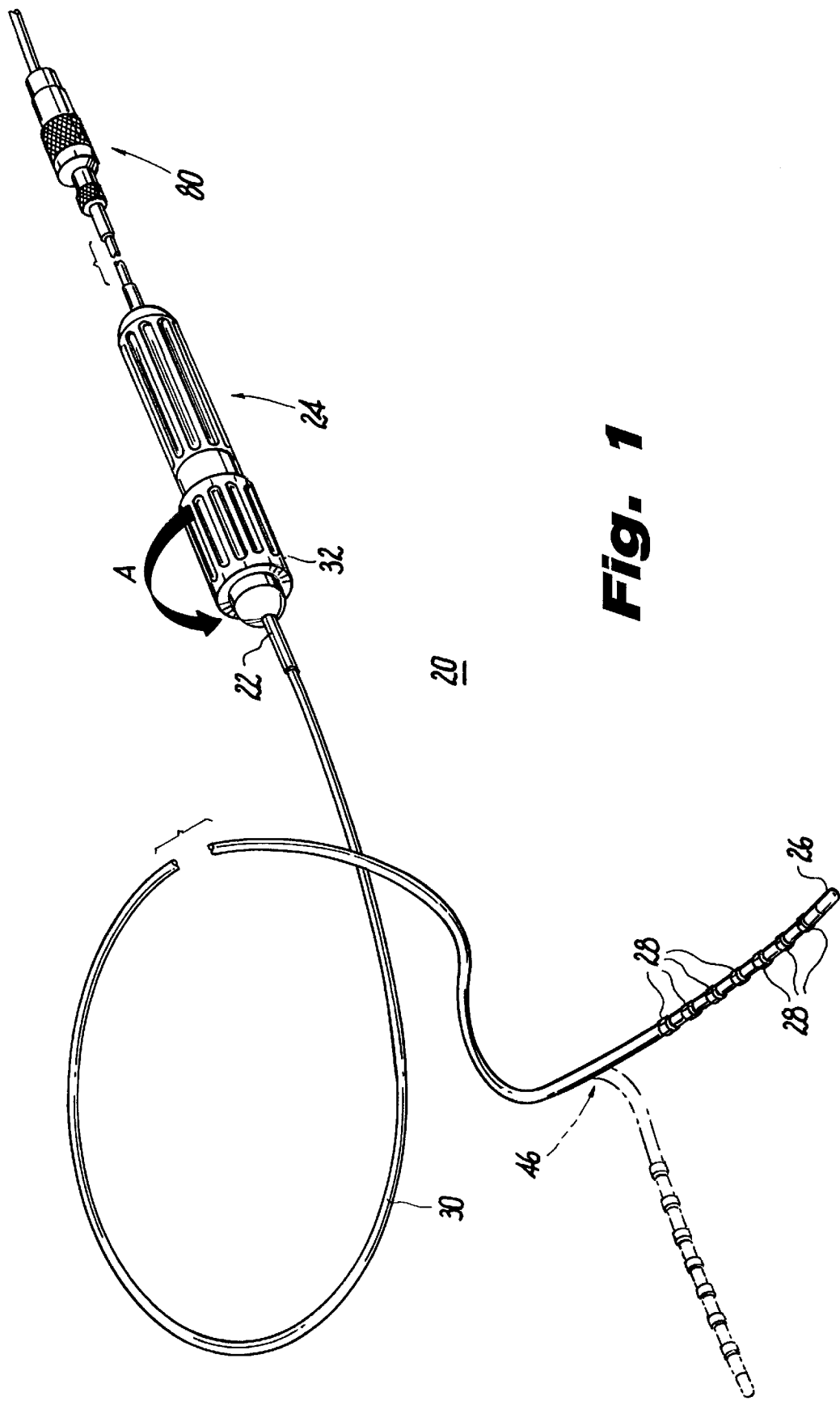
FIG. 1 is an elevational view of an electrode catheter embodiment constructed in accordance with the invention.

By way of overview and introduction, FIG. 1 shows an electrode catheter 20 having a shaft 30 attached at a proximal end 22 to a control handle 24 and extending to complexly curved and steerable sections which facilitate bringing the electrodes 26, 28 into precise and continuous contact with tissue within a patient, for example, the inner wall of the right atrium (see FIGS. 6 and 7). The control handle forms no part of the present invention. A suitable control handle is described in U.S. patent application Ser. No. 08/518,521 of Bowden et al. for STEERABLE ELECTRODE CATHETER, filed Aug. 23, 1995, which is hereby incorporated by reference as if fully set forth in its entirety herein.

Figure 2:
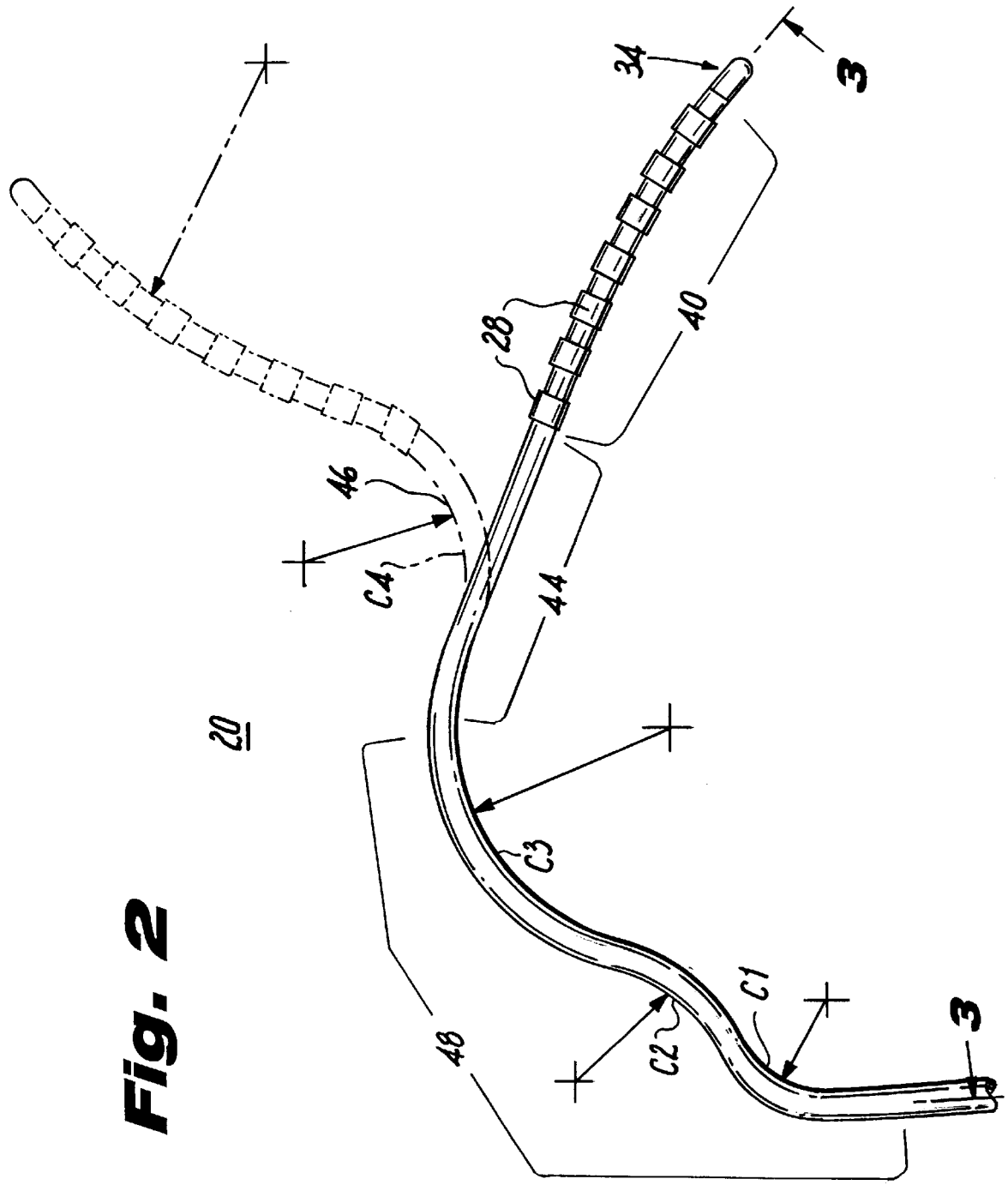
FIG. 2 is a plan view, partially in section, of the catheter of FIG. 1.

The control handle is manipulated, for example, to locate the distal end of the shaft 30 within the right atrium. A knob 32 on the control handle 24 is rotatable relative to the handle by the operator to cause a slideblock (not shown) within the control handle 24 to move away from the proximal end 22 of the shaft 30. A steering wire 38, which is slidably housed within the shaft 30 (see FIG. 3), is secured at its proximal end to the slideblock. The steering wire 38 is pulled proximally due to rotation of the knob 32, for example, in the direction of arrow A. Conversely, the steering wire 38 advances distally when the slideblock moves toward the proximal end 22 of the shaft 30 as a result of rotation of the knob 32 in the opposite direction. Preferably, the steering wire 38 is anchored to a distal tip assembly 34 (see FIG. 3), described below. A pulling force on the steering wire 38 causes the distal section of the catheter to be steered, as described next. The steering wire 38 must have a tensile strength sufficient to overcome the compressive strength of the shaft 30 to cause an intermediate section 44 to bend (FIG. 2). When the knob 32 is rotated in a direction opposite to arrow A, the compressive forces on the tip stock are released to cause the catheter tip to return to its relaxed, undeflected state. In the preferred embodiment, the steering wire 38 is a stainless steel wire having a pull strength of about 15.5 pounds.

With reference now to FIG. 2, the electrode catheter 20 is shown in its relaxed configuration (solid lines) and in its fully steered configuration (phantom lines). A distal section 40 of the shaft 30 supports the distal tip assembly 34, ring electrodes 28, and temperature sensor(s) 78 and includes a preferably off-axis lumen for the steering wire 38 and the electrical conductors for the electrodes 26, 28 and temperature sensors. The distal section 40 is preshaped to generally correspond to the physiology of the tissue to be mapped or ablated, for example, to have a radius corresponding to the radius of the inner wall of the right atrium. The shape may set into the material of the distal section of the shaft 30, or may be imparted to a hypotube 42 (FIG. 3), stiffening wire, or other elongate element capable of taking a set such as an element made of stainless steel or a shape memory alloy such as nickel-titanium. The shape of the distal section 40 is not affected by steering the catheter 20 to its fully steered configuration.

A flexible intermediate section 44 is disposed immediately proximal to the distal section 40. The intermediate section 44 bends or flexes at location 46 in response to a pulling force applied to the steering wire 38 to permit the shaft 30 to assume a partially or fully steered configuration (as shown in phantom). When the catheter 20 is fully steered, the intermediate section 44 bends to a radius of up to about 0.65 radian in a direction substantially opposite to the curve imparted to the distal section 40 and in substantially the same plane. Such bending is encouraged by the arrangement of the steering wire 38 within an off-axis lumen at least within the intermediate section 44 (see FIG. 3), and causes the distal section 40 to be urged into contact with tissue within the patient, for example, the inner wall of the right atrium.

A proximal section 48 extends proximally from the proximal end of the flexible intermediate section 44. The proximal section 48 includes a complex curve set in the shaft 30 which is shaped to seat the catheter relative to an anatomical feature within a patient. For example, the complex curve may be shaped to seat the catheter 20 across the annulus of the tricuspid valve to prevent prolapse of the catheter through the tricuspid valve, and is preferably shaped to contact generally opposing margins of the annulus of the tricuspid valve of the heart. This may be achieved by setting a series of curves C1–C3 which extend in substantially one plane generally as a sinusoid. Preferably, the curves C1–C3 are set into the material of the catheter by a baking process which provides a set which is retained at and somewhat above body temperature (37° C.).

As shown in the embodiment of FIG. 2, a first curve C1 has its origin on the right side of the catheter 20 and traces a 0.30 to 0.50 rad curve, a second curve C2 has its origin on the left side of the catheter 20 and traces a 0.30 to 0.50 rad curve, a third curve C3 has its origin on the right side of the catheter 20 and traces a 0.85 rad curve.

A fourth curve C4 is imparted to the catheter 20 having its origin on the left side of the catheter only when a force is applied to the steering wire 38 to steer the catheter 20. When fully steered, the curve C4 traces a 0.65 rad curve. This is due to the flexible intermediate section 44 having a comparatively greater flexibility than the proximal section 48 and the relative inflexibility of the distal section 40. As a result, substantially all of the flex in the catheter 20 in response to a pulling force applied to the steering wire 38 is accommodated by bending in the flexible intermediate section 44. The hypotube or stiffening wire 42 makes the distal section relatively inflexible. The flexible intermediate section 44 can be made comparatively more flexible than the proximal section 48 by providing a woven braid 56 from the proximal end 22 of the shaft 30 to the distal end of the proximal section 44. The braid 56 enhances the stiffness and torsional strength of the shaft 30. Thus, the proximal section 48 and the intermediate section 44 can both be made of the same material, and preferably, can both be made of polyurethane.

The distal section 40, flexible intermediate section 44, and the proximal section 48 are each intended to be inserted within the right atrium of the heart, as shown in FIGS. 6 and 7.

Turning now to FIGS. 3–5, portions of the catheter that are to be inserted into the right atrium are shown in cross section. The steering wire 38 is shown anchored to a core 50 of the distal assembly 34 by threading the steering wire through a lumen in the core 50 and back through another lumen after which the steering wire 38 is wrapped about itself. The steering wire 38 extends proximally through an off-axis lumen 52 (with respect to the longitudinal axis of the catheter 20) in the flexible intermediate section 44 to the slideblock in the control handle 24. (A teflon sheath 54 may surround the steering wire 38 to reduce friction through the lumen 52, as shown in FIG. 4.) The eccentric arrangement of the steering wire in the lumen 52 causes the catheter 20 to favor deflection in a known plane due to a wall thickness differential on either side of the steering wire 38 in the intermediate section 44. The entire control handle 24 can be torqued by the operator 35 to steer the shaft 30 through the patient's vasculature. Additional steering wires can be provided, and a radius of curvature adjusting means can be provided in the manner described in the aforementioned U.S. patent application Ser. No. 08/518,521.

The steering wire preferably is fixedly attached to the distal tip section as fully described in U.S. patent application Ser. No. 08/555,847 of Falwell et al. for SNAP FIT DISTAL ASSEMBLY FOR AN ABLATION CATHETER, filed Nov. 10, 1995, which is hereby incorporated by reference as if set forth in its entirety herein. It is sufficient, however, to attach the steering wire to other points within the distal section 40, provided the entire distal section 40 may be urged into contact with the inner wall of the right atrium. Because the steering wire is anchored to the distal tip section through an off-axis lumen 52, a proximal pulling force on the steering wire 38 causes the distal section 40 to deflect in a single plane along a single axis. The generally rigid hypotube 42 within the distal section 40 prevents the distal tip section from changing its shape in any substantial amount upon steering the tip assembly. Instead, the T5 catheter undergoes bending in the region of point 46 (FIG. 2) along the flexible intermediate section 44.

Turning again to FIG. 3, the distal section 40 of the shaft 30 terminates at distal tip 58. A central bore 60 in the distal tip 58 is sized to receive the proximal end 62 of the core 50 portion of the distal tip assembly 34. The core 50 has a compressible head 64 at its distal end which includes anchor tabs 66a, 66b. The core 50 has a longitudinal slot 68 extending proximally from its distal face which permits the anchor tabs 66a, 66b to resiliently flex toward each other as the core 50 is received within an aperture 70 in a hollow ablation electrode 26. Continued insertion of the core 50 into the ablation electrode 26 causes the anchor tabs 66a, 66b to snap into an annular groove 72 in the ablation electrode 26 which locks the core 50 and the ablation electrode 26 together. Due to tolerance control or other design considerations, the head 64 may remain in a partially compressed state even after the core and ablation electrode have snapped together so long as the two components interlock. The compressible head 64 includes a chamfered leading edge 74 which facilitates insertion of the core 50 into the aperture 70 of the ablation electrode 26 by camming the anchor tabs 66a, 66b together and thereby compressing the head 64 to a reduced profile. The annular groove 72 has a shoulder 76 at its proximal edge which prevents the core 50 from being withdrawn from the ablation electrode 26 once the anchor tabs 66a, 66b have snapped into the groove 72. Alternatively, equivalent snap-lock arrangements can be provided as described in the aforesaid U.S. Pat. No. 08/555,847 application.

The core 50 is preferably made of a material having a low temperature coefficient, such as the ULTEM® 1000 resin produced by the GE Plastics division of the General Electric Company, Pittsfield, Mass. The low temperature coefficient material provides thermal insulation between the ablation electrode 26 and the distal section 40. The provision of the core 50 between the distal section 40 and the ablation electrode 26 reduces the likelihood of catheter damage during an ablation procedure. As a result, a wider range of materials can be selected for the distal section 40, including materials with melt-temperatures that are significantly less than the expected ablation temperature, such as polyurethane.

With further reference to FIG. 3, the distal assembly 34 preferably houses a temperature sensor 78. As described in the aforesaid U.S. Pat. No. 08/555,847 application, the core 50 includes a central lumen and several off-axis lumens for conveying wires from the ablation electrode 26 and the temperature sensor 78, respectively, to a conventional connector 80 (FIG. 1). The temperature sensor 78 is preferably a thermistor and may be positioned within a cavity 82 in the ablation electrode 26 about four to seven mils from the ablation electrode distal tip. A potting compound 84, for example, TRA-BOND FDA-2 epoxy made by Tra-Con, Inc. of Medford, Mass. may add rigidity to the entire distal assembly 34.

The distal section 40 defines a lumen 86 for receiving the steering wire 38 and its surrounding teflon sheath 54 (FIGS. 4 and 5), as well as the conductive wires from the temperature sensor 78 and the distal ablation electrode 26. Mounted in spaced relation along the distal section 40 are ring electrodes 28a, 28b, and 28c which may be sized for intracardiac ECG recording, mapping, stimulation, or ablation. The ring electrodes 28 are electrically connected to suitable components via conductive wires 88a, 88b, and 88c which extend through respective apertures 90a–c in the side of the distal section 40 into the lumen 86. The lumen 86 communicates with the off-axis lumen 52 in the intermediate section 44 and also may be provided as an off-axis lumen.

The ring electrodes 28a–c are individually connected to a recording and monitoring device via conductive wires 88a–c. Each ring electrode may have a temperature sensor associated with it to provide temperature sensing at the surface of the electrodes in the same manner as temperature sensor 78 is provided for the electrode 28. The temperature sensors are connected to a generator via similar electrical conductors. In operation, a signal may be sent from the temperature sensors to the generator to either increase or decrease the supplied radiofrequency ("RF") energy. This enables the temperature of the ablation to be maintained at a preset level.

The distal section 40 may be integral with the intermediate section 44. In the preferred embodiment, the proximal section 40 includes the woven braid 56, and this section may be connected to the proximal end of the intermediate section 44 in a conventional manner, preferably along complementary tapered and overlapping regions at their respective distal and proximal ends, respectively, for example, as shown at 92 (FIG. 3). This may be achieved, for example, by ultrasonic welding. A lumen 94 in the proximal section 48 extends proximally to the control handle 24, and is in communication with the off-axis lumen 52 of the intermediate section 44 and the lumen 86 of the distal section 40.

The ring electrodes and the tip electrode are preferably made from platinum. Each electrical conducting wire is separately electrically insulated to allow the conducting wires to share a single lumen through the catheter body. The conducting wires are preferably 0.005" diameter copper wire, with approximately 0.001" thick insulation thereon.

Figure 8:
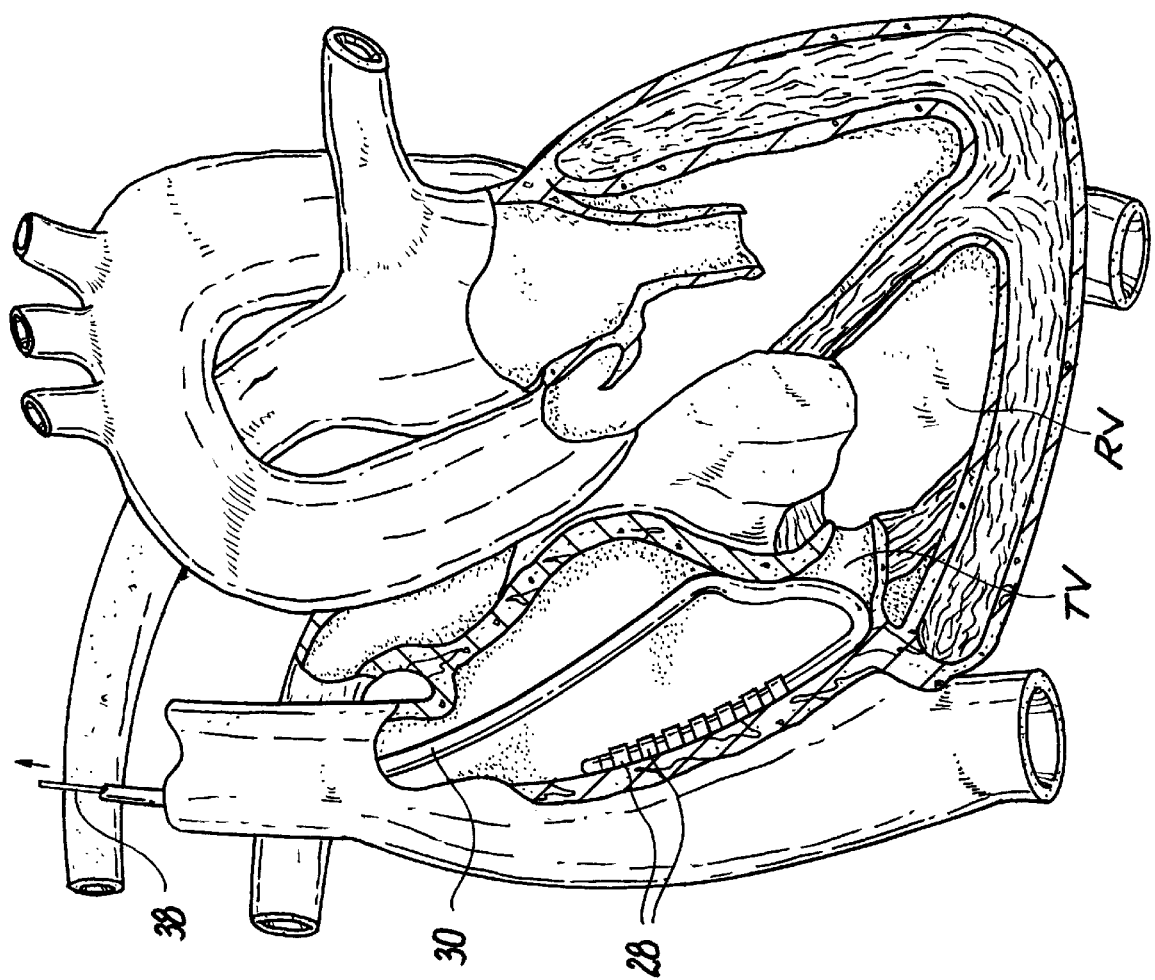
FIG. 8 is a view of the right atrium of the heart with parts broken away showing the catheter of FIG. 1 having a section seated across the annulus of the tricuspid valve and another section located against the inner wall of the right atrium.

In operation, the catheter 20 may be advanced into the right atrium, for example, from the superior vena cava. The distal section 40 is generally advanced toward the right atrium by applying a pulling force on the steering wire 38 (for example, by rotating the knob 32 of the control handle 24) to generally align the distal section 40 with the longitudinal axis of the shaft 30 by bending the flexible intermediate section 44 at point 46 (FIG. 6). Once the proximal section 48 has entered the right atrium RA, the pulling force is released so that the intermediate section 44 is no longer bent at point 46 (FIG. 7). With the catheter 20 is in its relaxed condition, the proximal, intermediate, and distal sections 48, 44, and 40 generally assume a J-shaped configuration, with the distal section 40 being oriented more toward the superior vena cava SVC than the inferior vena cava IVC. The catheter is then advanced into contact with the atrioventricular septum which separates the right atrium RA and the right ventricle RV (FIG. 8). The complex curvature of the proximal section 44 is shaped to seat or nest the catheter 20 across the annulus of the tricuspid valve TV, which valve permits communication between the right atrium RA and the right ventricle RV. The seated catheter automatically locates the distal section 40 and the electrodes 26, 28 within the right atrium, adjacent the inner wall thereof. Once seated, the catheter 20 cannot prolapse through the tricuspid valve into the right ventricle. A pulling force is then applied to the steering wire 38 to urge the electrodes 26, 28 into firm contact with the cardiac tissue, as shown by the arrow alongside the steering wire 38 in FIG. 8. Good tissue contact can be determined by impedance measurements in a manner well known in the art. When good tissue contact is achieved, RF energy is applied to the distal tip and ring electrodes. RF energy is then turned off and the catheter can then be rotated with respect to an axis of the tricuspid valve so that said distal section 40 can be positioned into contact with different portions of the inner wall of the right atrium for further mapping and/or ablation. The seated proximal section 48 thus provides a reference point relative to the patient's anatomy which ensures that the ring electrodes 28 are placed accurately within the right atrium.

In the preferred embodiment, a plurality of conductive ring electrodes are mounted on the outer surface of the distal section 40. The ring electrodes 281 are typically 4 mm in length with 3 mm spacing between the ring electrodes. It is understood that the actual sizes of the ring electrodes and the spacing between the ring electrodes may be varied depending on the specific intended use for the catheter. The outer diameter of the electrodes is preferably substantially equal to the outer diameter of the distal section 40 so that the electrodes form a substantially smooth, continuous surface with the outer surface of the distal section 40.

As will be readily apparent to those skilled in the art the dimensions stated relate to one particular catheter size and are disclosed solely by way of example and should not, therefore, be understood as an intended limitation on the scope of the invention. For example, the radii of curvature and electrode spacings may be varied to suit individual patient needs as function of the dimensions of the patient's heart and surrounding anatomy.

Any one or more of these alternative embodiments may be combined one with another for a particular use contemplated or intended for a tip deflectable, steerable ablation catheter. For example, the catheter can have a relaxed condition as shown in phantom in FIGS. 1 and 2 and a fully steered condition as shown in solid lines in the same figures. According to this alternative arrangement, the off-axis lumen 52 preferably would be located on the opposite side from that shown in FIG. 3.

Furthermore, the particular features described above can be arranged on different elements to achieve a flexible and steerable catheter within the spirit of the foregoing disclosure, including steerable catheters having an angioplasty balloon supported thereon instead of electrodes, or any one (or more) of a variety of other devices for performing a medical procedure.

While the invention has been particularly shown and described with reference to a preferred embodiment thereof, it will be understood by those skilled in the art that various changes in form and details may be made therein without departing from the spirit and scope of the invention.

What is claimed is:

1. A steerable catheter for insertion within a heart of a patient, comprising:

a distal section shaped to generally correspond to the physiology of an inner wall of the heart, a flexible intermediate section having a distal end connected to said distal section, a complexly curved proximal section having a distal end connected to said flexible intermediate section, said proximal section being shaped to seat the catheter relative to an anatomical feature within the heart, said proximal section, flexible intermediate section, and distal section each being insertable within the heart, and means for steering the distal section of the seated catheter into contact with the inner wall of the heart by flexing said flexible intermediate section.

2. The steerable catheter as in claim 1, wherein said proximal section is shaped to contact generally opposing margins of the annulus of the tricuspid valve of the heart.

3. The steerable catheter as in claim 2, wherein the catheter is rotatable with respect to an axis of the tricuspid valve so that said distal section can be steered into contact with different portions of the inner wall of the right atrium.

4. The steerable catheter as in claim 1, wherein said complexly curved proximal section includes first and second curves extending in a first longitudinal direction and a third curve therebetween extending in a second longitudinal direction which is substantially opposite said first longitudinal direction, a fourth curve being formed in said second longitudinal direction due to flexing of said flexible intermediate section in response to steering of said distal section.

5. The steerable catheter as in claim 1, wherein the catheter is an electrode catheter and wherein said distal section supports a plurality of spaced electrodes.

6. The steerable catheter as in claim 1, wherein said preshaped distal section includes a preshaped hypotube.

7. The steerable catheter as in claim 1, wherein said complexly curved proximal section is curved in substantially one plane.

8. The steerable catheter as in claim 1, wherein said steering means includes a steering wire connected to said distal section which causes said flexible intermediate section to flex in response to an applied pulling force.

9. The steerable catheter as in claim 8, wherein said flexible intermediate section has a comparatively greater flexibility than said complexly curved proximal section, whereby substantially all of the flex in the catheter in response to the applied pulling force is contained within said flexible intermediate section.

10. The steerable catheter as in claim 8, wherein said flexible intermediate section includes an off-axis lumen which houses said steering wire.

* * * * *